US00PP23897P2

(12) United States Plant Patent
Laist

(10) Patent No.: US PP23,897 P2
(45) Date of Patent: Sep. 10, 2013

(54) *CALIBRACHOA* PLANT NAMED 'J-1'

(50) Latin Name: ***Calibrachoa* sp.**
Varietal Denomination: J-1

(76) Inventor: Michal Laist, Bene-Atarot (IL)

( * ) Notice: Subject to any disclaimer, the term of this patent is extended or adjusted under 35 U.S.C. 154(b) by 444 days.

(21) Appl. No.: 12/924,814

(22) Filed: Oct. 6, 2010

(51) Int. Cl.
*A01H 5/00* (2006.01)

(52) U.S. Cl.
USPC ..... Plt./413

(58) Field of Classification Search
USPC ..... Plt./413
See application file for complete search history.

*Primary Examiner* — June Hwu
(74) *Attorney, Agent, or Firm* — Mark P. Bourgeois

(57) ABSTRACT

A new cultivar of *Calibrachoa* plant named 'J-1' that is characterized by double red-purple flowers, vigorous growth and early flowering.

1 Drawing Sheet

Botanical classification: *Calibrachoa* sp.
Variety denomination: 'J-1'.

BACKGROUND OF THE INVENTION

The present invention relates to a new and distinct cultivar of *Calibrachoa* plant botanically known as *Calibrachoa* sp. and hereinafter referred to by the cultivar name 'J-1'.

'J-1' is a naturally occurring branch mutation of a proprietary *Calibrachoa* cultivar 'I-11' (not patented). 'J-1' was discovered in a greenhouse in a cultivated area of Bnei-Zion, Israel in December of 2009.

Asexual reproduction first occurred when terminal cuttings of the new cultivar 'J-1' were propagated in December of 2009 in Bnei-Zion, Israel. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Calibrachoa* cultivar 'J-1'. These traits in combination distinguish 'J-1' as a new and distinct cultivar apart from other existing known varieties of *Calibrachoa*.

1. *Calibrachoa* 'J-1' exhibits double red-purple flowers.
2. *Calibrachoa* 'J-1' exhibits vigorous growth.
3. *Calibrachoa* 'J-1' exhibits early flowering.

The closest comparison cultivar is the parent plant *Calibrachoa* 'I-11'. The new cultivar 'J-1' is distinguishable from the parent *Calibrachoa* 'I-11' by the following characteristics:

1. 'J-1' exhibits a large central flower whorl. The flowers of 'I-11' do not have a central flower whorl.
2. 'J-1' exhibits lighter color flowers than 'I-11'.

BRIEF DESCRIPTION OF THE DRAWING

The accompanying photograph illustrates the distinguishing traits of *Calibrachoa* 'J-1'. The plant in the photograph shows an overall view of a 3.5 month old plant.

The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Calibrachoa* cultivar named 'J-1'. Data was collected in Ben-Zion, Israel from 3.5 month plastic greenhouse grown plants in 12 cm containers. The time of year was Winter. The average temperature during the day was 22° Centigrade and 15° Centigrade at night. The average light level was 700 Lux. Color determinations are in accordance with The Royal Horticultural Society Colour Chart 2001 edition, except where general color terms of ordinary dictionary significance are used. The growing requirements are similar to the species. 'J-1' has not been tested under all possible conditions and phenotypic differences may be observed with variations in environmental, climatic, and cultural conditions, however, without any variance in genotype.

Botanical classification: *Calibrachoa* sp. 'J-1'.
Annual or perennial: Annual.
Use: Ornamental.
Parentage: 'J-1' is a naturally occurring branch mutation of *Calibrachoa* 'I-11'.
Vigor: Strong.
Overall shape: Mounded with trailing habit.
Height: 35 cm. in height.
Width: 40 cm. in width.
Low temperature tolerance: 2 to 3 degrees Centigrade.
High temperature tolerance: 36 degrees Centigrade.
Propagation: Terminal cuttings.
Time to initiate roots (summer): 10 days.
Time to initiate roots (winter): 16 days.
Time to produce a rooted cutting or liner (summer): 20 days.
Time to produce a rooted cutting or liner (winter): 26 days.
Crop time: 6 weeks are required to produce a flowering plant.
Root system: Fine and fibrous.
Stem:
*Branching habit.*—Basal.
*Average number of lateral branches.*—12.
*Pinching.*—No.
*Lateral branch diameter.*—5-6 mm. in diameter.
*Lateral branch length.*—3 cm. in length.
*Stem color.*—137B.

*Stem shape.*—Round.
*Stem texture.*—Smooth.
*Stem strength.*—Strong.
*Pubescence.*—Absent.
*Internode length.*—3-4 mm.

Foliage:
*Leaf arrangement.*—Alternate.
*Compound or single.*—Single.
*Quantity of leaves per lateral branch.*—Approximately 16.
*Leaf shape.*—Linear.
*Leaf apex.*—Obtuse.
*Leaf base.*—Attenuate.
*Leaf length.*—33-35 mm. in length.
*Leaf width.*—5-6 mm. in width.
*Texture.*—Both sides glabrous.
*Pubescence.*—Very fine hairs on upper side only.
*Leaf margin.*—Entire.
*Young leaf color* (*lower surface*).—138A.
*Young leaf color* (*upper surface*).—137A.
*Mature leaf color* (*lower surface*).—138A.
*Mature leaf color* (*upper surface*).—137A.
*Vein color* (*lower surface*).—138A.
*Vein color* (*upper surface*).—137A.
*Venation pattern.*—Pinnate.
*Leaf attachment.*—Sessile.

Flower:
*Flower arrangement.*—Double salverform flowers arising from leaf axils.
*Quantity of flowers per lateral stem.*—Approximately 8.
*Quantity or flower buds per lateral stem.*—Approximately 8.
*Flowering season.*—Continuous.
*Fragrance.*—None.
*Flower bud length.*—18 mm. in length.
*Flower bud diameter.*—8 mm. in diameter.
*Flower bud shape.*—Tubular.
*Bud color.*—70B.
*Flower aspect.*—Outward.
*Flower dimensions.*—27-28 mm. in diameter and 25-26 mm. in length.
*Flower tube dimensions.*—2-6 mm. in diameter and 1.7 cm. in length.
*Flower longevity on plant.*—Approximately 4-5 days.
*Petal arrangement.*—5 petals fused into funnel shape.
*Petal texture.*—Glabrous both sides.
*Fused or unfused.*—Fused.
*Petal shape.*—Obovate.
*Petal margin.*—Entire.
*Petal apex.*—Obtuse.
*Petal color when opening* (*upper side*).—N74A.
*Petal color when opening* (*under side*).—70C.
*Petal color fully opened* (*upper side*).—N74B.
*Petal color fully opened* (*under side*).—72C.
*Flower tube color inner surface.*—1A with stripes 178B.
*Flower tube color outer surface.*—1C with stripes 178B.
*Petaloid number.*—5.
*Petaloid shape.*—Obovate.
*Petaloid dimensions.*—11 mm. in length and 3 mm. in width.
*Petaloid texture.*—Smooth both surfaces.
*Petaloid color when opening* (*upper side*).—N74A.
*Petaloid color when opening* (*under side*).—70C.
*Petaloid color fully opened* (*upper side*).—N74B.
*Petaloid color fully opened* (*under side*).—72C.
*Self-cleaning or persistent.*—Persistent.

Sepals:
*Number of sepals.*—Five.
*Sepal shape.*—Linear.
*Sepal margin.*—Entire.
*Sepal apex.*—Acute.
*Sepal base.*—Fused.
*Sepal surface.*—Smooth both sides.
*Sepal dimensions.*—13 mm. in length and 2 mm. in width.
*Sepal color* (*upper side*).—137A.
*Sepal color* (*under side*).—137D.

Calyx:
*Calyx shape.*—Bell shaped.
*Calyx dimensions.*—15 mm. in length and 6 mm. in diameter.

Reproduction organs:
*Stamen.*—None.
*Pistil number.*—3 to 4.
*Stigma shape.*—Elongated.
*Stigma color.*—138C.
*Style length.*—6-7 mm.
*Style color.*—138C.

Fruit/seed production: Produces no seeds.

Disease and pest resistance: Resistance to diseases and or pests has not been observed.

The invention claimed is:

1. A new and distinct variety of *Calibrachoa* plant named 'J-1' as described and illustrated.

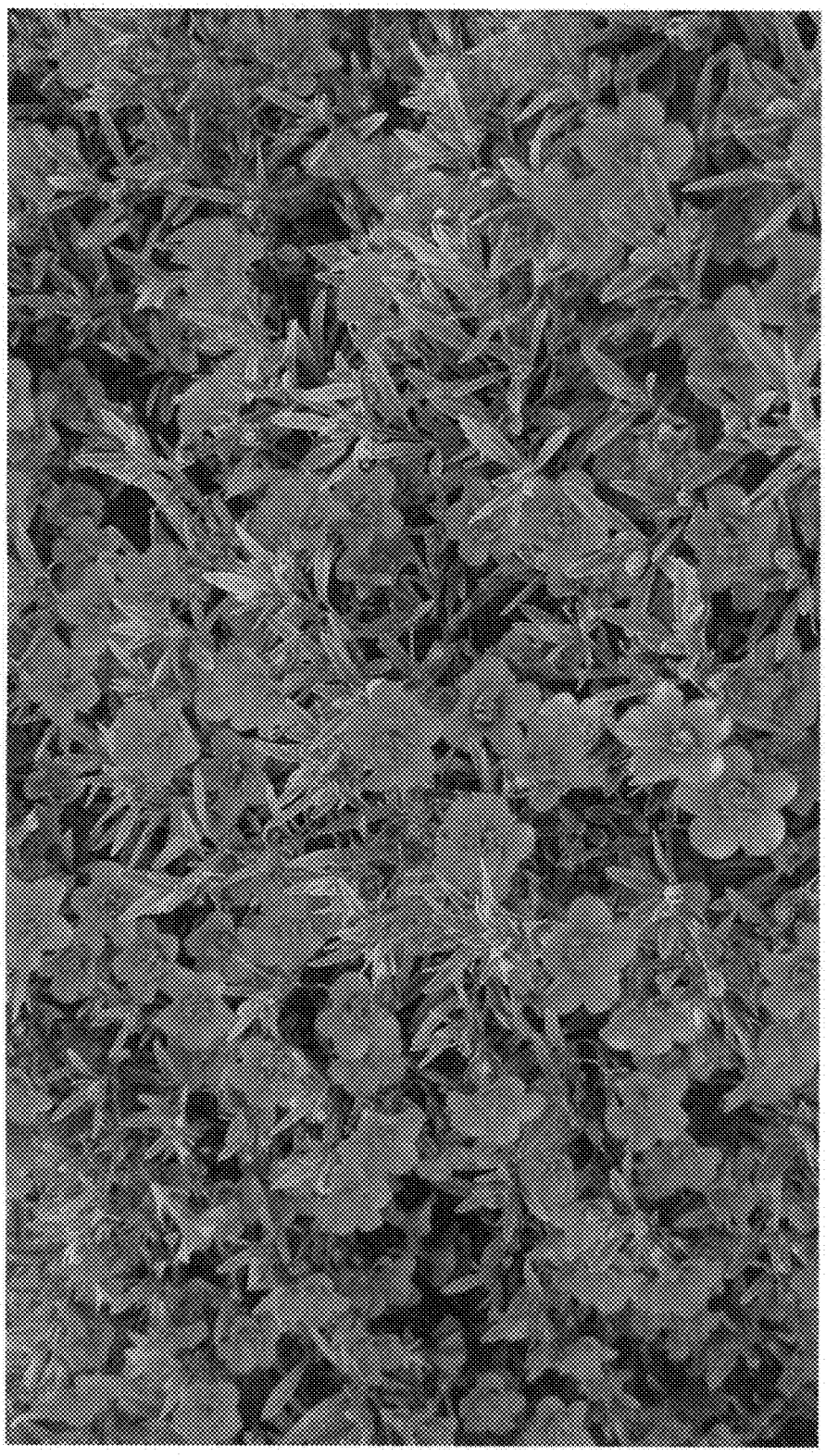

* * * * *